(12) United States Patent
Garnham et al.

(10) Patent No.: US 9,144,677 B2
(45) Date of Patent: *Sep. 29, 2015

(54) VESTIBULAR IMPLANT SYSTEM WITH INTERNAL AND EXTERNAL MOTION SENSORS

(71) Applicant: MED-EL Elektromedizinische Geraete GmbH, Innsbruck (AT)

(72) Inventors: Carolyn Garnham, Matlock (GB); Martin Zimmerling, Patsch (AT); Andreas Jäger, Reith bei Seefeld (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

This patent is subject to a terminal disclaimer.

(21) Appl. No.: 14/464,986

(22) Filed: Aug. 21, 2014

(65) Prior Publication Data

US 2014/0364922 A1    Dec. 11, 2014

Related U.S. Application Data

(63) Continuation of application No. 14/014,502, filed on Aug. 30, 2013, now Pat. No. 8,843,204, which is a continuation of application No. 13/187,979, filed on Jul. 21, 2011, now abandoned.

(60) Provisional application No. 61/366,345, filed on Jul. 21, 2010.

(51) Int. Cl.
*A61N 1/36* (2006.01)
*A61B 5/11* (2006.01)
*A61B 5/00* (2006.01)
*A61N 1/372* (2006.01)
*A61N 1/375* (2006.01)

(52) U.S. Cl.
CPC .............. *A61N 1/36032* (2013.01); *A61B 5/11* (2013.01); *A61B 5/6817* (2013.01); *A61B 5/6867* (2013.01); *A61N 1/375* (2013.01); *A61N 1/37211* (2013.01); *A61B 5/6814* (2013.01); *A61B 2562/0219* (2013.01)

(58) Field of Classification Search
CPC ...... A61B 5/6817; A61B 5/6887; A61B 5/11; A61B 5/6814; A61N 1/37211; A61N 1/36032
USPC ..................................................... 607/55–57
See application file for complete search history.

(56) References Cited

U.S. PATENT DOCUMENTS

| | | | |
|---|---|---|---|
| 5,749,912 | A | 5/1998 | Zhang et al. |
| 6,138,681 | A | 10/2000 | Chen et al. |
| 7,225,028 | B2 | 5/2007 | Della Santina et al. |
| 8,241,296 | B2 | 8/2012 | Wasielewski |
| 2003/0195588 | A1 | 10/2003 | Fischell et al. |

*Primary Examiner* — Amanda Patton
(74) *Attorney, Agent, or Firm* — Sunstein Kann Murphy & Timbers LLP

(57) ABSTRACT

A vestibular prosthesis system is described which includes an external movement sensor that is attachable a patient's head for generating an external movement signal. A fail-safe sensor is configured to detect movement of the one or more external movement sensors relative to the head and generate a corresponding relative motion signal. And an implant processor also is implantable under the skin and in communication with the fail-safe sensor and the external transmitter for generating an implant stimulation signal based on the external movement signal and/or the relative motion signal to electrically stimulate target neural tissue for vestibular sensation by the patient.

15 Claims, 9 Drawing Sheets

VESTIBULAR IMPLANT SYSTEM WITH INTERNAL AND EXTERNAL MOTION SENSORS

This application is a continuation of U.S. patent application Ser. No. 14/014,502, filed Aug. 30, 2013, which in turn is a continuation of U.S. patent application Ser. No. 13/187,979, filed Jul. 21, 2011, which claims priority from U.S. Provisional Patent Application 61/366,345, filed Jul. 21, 2010, which is incorporated herein by reference.

TECHNICAL FIELD

The present invention relates to implantable stimulation systems, and more specifically to a vestibular implant system with internal and external motion sensors.

BACKGROUND ART

A normal ear directs sounds as shown in FIG. 1 from the outer ear pinna 101 through the generally cylindrical ear canal 110 (typically about 26 mm long and 7 mm in diameter) to vibrate the tympanic membrane 102 (eardrum). The tympanic membrane 102 moves the bones of the middle ear 103 (malleus, incus, and stapes) that vibrate the cochlea 104, which in turn functions as a transducer to generate electric pulses to the brain that are interpreted as sounds. In addition, the inner ear also includes a balance sensing vestibular system which involves the vestibular labyrinth 105, its three interconnected and mutually orthogonal semi-circular canals: the superior canal 106, posterior canal 107, and horizontal canal 108 (as well as the otolith organs, the utricle and saccule—not shown). The canals and spaces of the vestibular labyrinth 105 are filled with endolymph fluid which moves relative to head movements, thereby activating hair cells that send an electrical balance signal to the brain via the vestibular nerve 111.

In some people, the vestibular system is damaged or impaired, causing balance problems such as unsteadiness, vertigo and unsteady vision. Vestibular implants are currently under development, with one of the initial challenges being the relatively significant amount of power required by the gyroscope/accelerometer arrays used for the movement sensors (gyroscopes and linear accelerometers). Presently, one lower power device is the STMicroelectronics L3G4200D, which is a three-axis digital gyroscope that encodes all three-dimensional axes of rotation. This device measures 4 mm square by 1 mm thick and needs various power and signal lines to operate at the specified power requirement of at least 6 mA at 3.6V.

For use in an implant system, the power for one or more vestibular movement sensors can be supplied from a body worn battery pack and transcutaneously transmitted with a head placed coil. But the power losses for such a transcutaneous supply are roughly a factor of two and there also is an additional risk of the head coil falling off, power being lost, and the patient becoming disoriented and even falling. A somewhat better solution might be to have an implanted battery supplying power to the implanted movement sensors, but (due to the high power requirements) this approach is likely to require a large battery volume or very frequent re-charging of the battery. Furthermore, failure of any of the modules of the device would require re-implantation, with consequent risk to hearing and residual vestibular function.

Other arrangements have also been proposed for vestibular implant systems. For example, head-worn sensor arrays have been proposed that would be secured by a holding band around the head, but this approach would create an unacceptably high risk of movement of the sensors relative to the head. Implanted sensor arrays powered via a percutaneous plug have also been proposed, but the serious problems with percutaneous structures are notoriously well-known. Challa and Bhatti, *A Micromachined Cupula: Toward Biomimetic Angular Velocity Sensor Prosthesis*, $33^{rd}$ Mid-Winter Research Meeting, Assn. for Research in Otolarygology, Feb. 6-10, 2010 (incorporated herein by reference) proposed a basic re-design of the sensor array around the fluidic principle used by the balance organ itself to reduce power requirements, but more time and extensive reliability testing will be needed to complete the development of such a device.

Application US2005/0267549 by Della Santina et al. (incorporated herein by reference) teaches a combined cochlea/vestibular stimulation system with a speech and motion sensing processor (SMP) placed either externally or internally. Application US2002/0104971 by Merfeld et al. (incorporated herein by reference) teaches a motion sensing system to be worn not only on the head but also on other body parts.

For safety reasons, it is important that the externally worn unit including the sensor is always placed in a known, correct orientation when driving the implant. Otherwise the sensor's misaligned input to signal processing, and ultimately to the neural stimulation sites, will lead to a mismatch between real and perceived head movement. Under specific circumstances this may cause a patient to fall and possibly result in injury. This is of special relevance when the implant is located on the head such that sometimes the patient cannot visually observe placing the external unit over the implant.

The correct placement of an external unit relative to an implant is currently solved for cochlear implants and other auditory implants by a pair of axially magnetized magnets. One magnet is placed in the center of the implant's receiver coil. The other magnet is placed in the center of the sender coil in the external unit. While placing the external unit's magnet in proximity to that of the implant, the magnetic attraction force causes the external coil to be placed over the implant's coil in a concentric orientation. But there is a remaining degree of freedom in that the external unit can be turned in the radial direction a full 360 degrees relative to the implant. Due to this degree of radial rotation freedom, this solution is not appropriate for placing an external sensor as part of a vestibular implant system.

SUMMARY

Embodiments of the present invention are directed to a partially implantable vestibular prosthesis system which includes an external movement sensor module that is attachable to the outer skin surface of a patient's head for generating an external movement signal which represents movement of the patient's head. An external transmitter is in communication with the external movement sensor and provides an electromagnetic transmission of an implant communication signal which includes a signal component based on the external movement signal and an electrical power component that provides electrical power for the implanted system components. A fail-safe sensor is configured to detect movement of the one or more external movement sensors relative to the head and generate a corresponding relative motion signal. And an implant processor also is implantable under the skin and in communication with the internal movement sensor and the external transmitter for generating an implant stimulation signal based on the external movement signal and/or the relative motion signal to electrically stimulate target neural tissue such as the semicircular canals of the inner ear, the otolith organs, and/or the vestibular nerve for augmentation or modification of the patient's vestibular function.

In some specific embodiments, the external movement sensor may be adapted to be attachable within the ear canal of the patient's head. For example, the external movement sensor module may be magnetically attachable within the ear canal over a corresponding implanted holding magnet which establishes a correct position for the external movement sensor. The external movement sensor module also may be adapted to leave a portion of the ear canal unoccluded to allow hearing sensation by the tympanic membrane. In other embodiments, the external movement sensor module may be magnetically attachable on the scalp of the patient's head over a corresponding implanted holding magnet which establishes a correct position for the external movement sensor module.

For example, the external movement sensor module may include multiple magnets for cooperation with corresponding multiple magnets in the implant magnet arrangement. In such an embodiments, the magnets in the external movement sensor may be arranged with asymmetrical magnetic polarities, with spatial asymmetry, with asymmetrically different diametrical orientations, and/or with asymmetrically different distances between cooperating pairs of magnets. And the magnets in the external movement sensor may be arranged to require orientation of the external movement sensor so that each magnet in the external movement sensor is cooperating with another corresponding magnet in the implant magnet arrangement in order to have enough magnetic attraction force to securely hold the external movement sensor. The implant processor may include a baseline pacing mode wherein the implant stimulation signal is generated without reference to a movement signal.

DETAILED DESCRIPTION

Embodiments of the present invention are directed to a safe, practicable and wearable partially implantable vestibular prosthesis system which combines both internal and external movement sensors. By making appropriate design choices, many of the drawbacks from earlier approaches can be avoided. For example, in some embodiments the internal implant movement sensor can be mainly used as a backup signal source for a few hours (depending on the battery life of the implant battery) when the main externally worn movement sensor is unavailable or unreliable. Other embodiments may use an implanted movement sensor as its normal main signal source, with an external movement sensor serving as a system backup signal source in the event of failure by the implanted movement sensor.

Figure 1:
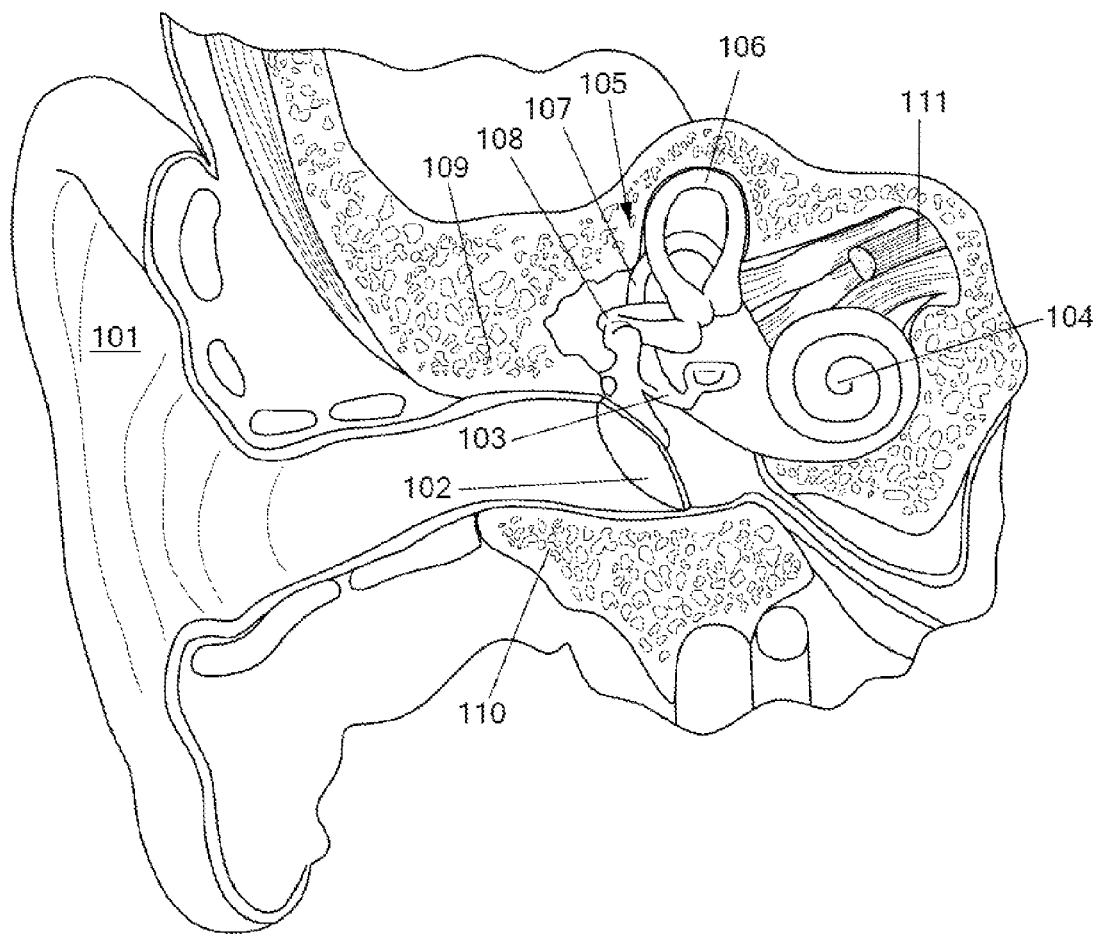
FIG. 1 shows various anatomical structures associated with the human ear.
Figure 2:
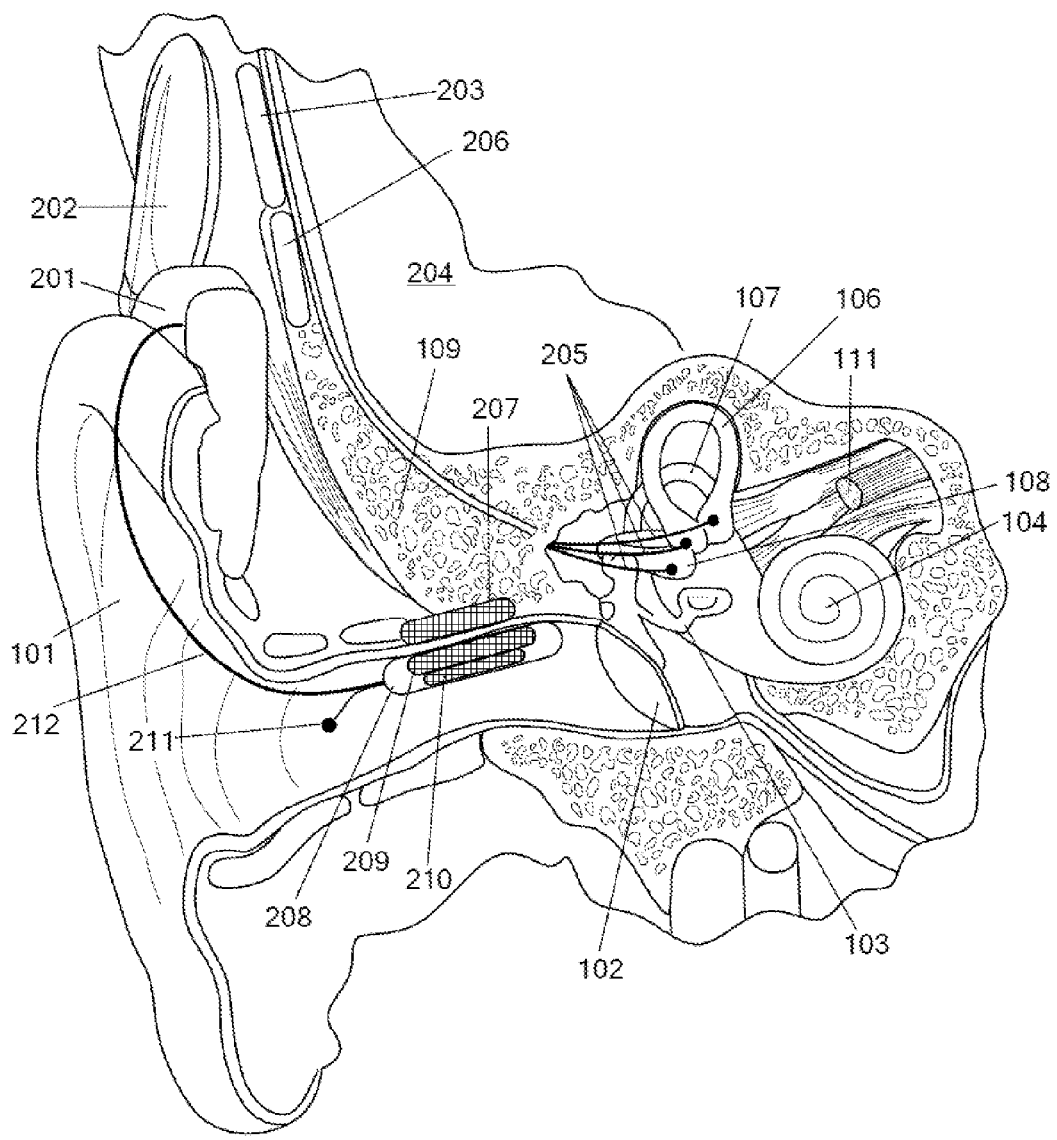
FIG. 2 shows one specific example of a partially implantable vestibular prosthesis system.

FIG. 2 shows one specific example of a partially implantable vestibular prosthesis system with an external movement sensor 208 that includes a three-axis digital gyroscope array 210 that generates an external movement signal encoding three-dimensional axes of rotation representing movement of the user's head. The external movement sensor 208 is adapted to be positioned within the ear canal 110 of the user where an attachment magnet 209 within the external movement sensor 208 cooperates with a corresponding implanted holding magnet 207 that is surgically implanted under the skin of the ear canal 110.

An external movement sensor 208 that fits in the ear canal 110 also is well-suited for mild to moderately deaf patients (who make up quite a large number of patients with vestibular problems) and might be incorporated together with a hearing implant, or it might be matched with hearing or a hearing aid on the other side, and/or might include a sound channel or large vent to partially transmit sound for patients with hearing in that ear. Locating the external movement sensor 208 deep in the bony section of the ear canal 110 provides a low probability of many movement artifacts and a low risk of being displaced by normal activities. This is in contrast to a more shallow location in the lower anterior portion of the ear canal 110 where jaw movements may cause unacceptable movement artifacts. An ideal location for external movement sensor 208 may be as shown in FIG. 2, fixed in place (e.g., with a retaining magnet) adjacent to the posterior, superior potion of the canal wall, deep in the bony section of the ear canal 110. Adverse effects of jaw movements will be minimized using this location and may be further minimized through use of a partially occluding design or a flexible occluding volume.

For hearing patients, the external movement sensor 208 normally should take up as little room as possible in the ear canal 110 to allow adequate transmission of sound to the tympanic membrane 102. It may be advantageous if the external movement sensor 208 is adapted to leave a portion of the ear canal 110 unoccluded as shown in FIG. 2 to allow relatively normal hearing sensation by the tympanic membrane 102.

Alternatively, the external movement sensor 208 could be incorporated into a very deep canal fitting device such as a Lyric-type hearing aid device which fits deeply within the ear canal 110 nearer the tympanic membrane 102. For hearing patients, the option of a deep canal fitting may be especially suitable if designed to allow adequate transmission of sounds to the tympanic membrane 102.

In another embodiment, some portion of the external movement sensor 208 would need to be fitted snugly deep into the ear canal 110 for stability, but the external end of the ear canal 110 could still be available for other uses such as other system components. Additional device-related components then could be connected to the deeply fitted part by a very flexible cable. For example, power supply and signal processing components also could be located within the outer portion of the ear canal 110 and be connected to the external movement sensor 208 by a very flexible connector.

The external movement sensor 208 is connected by a connector lead 212 to a behind-the-ear external processor 201. It is advantageous if the connector lead 212 is very flexible so that small movements of the outer ear 101 and/or the external processor 201 (such as for programming) do not disturb the fit and position of the external movement sensor 208 in the ear canal 110. A handling member 211 also projects out of the external movement sensor 208 to aid the user's ability to remove the external movement sensor 208, e.g., for bathing or device maintenance.

Figure 4:
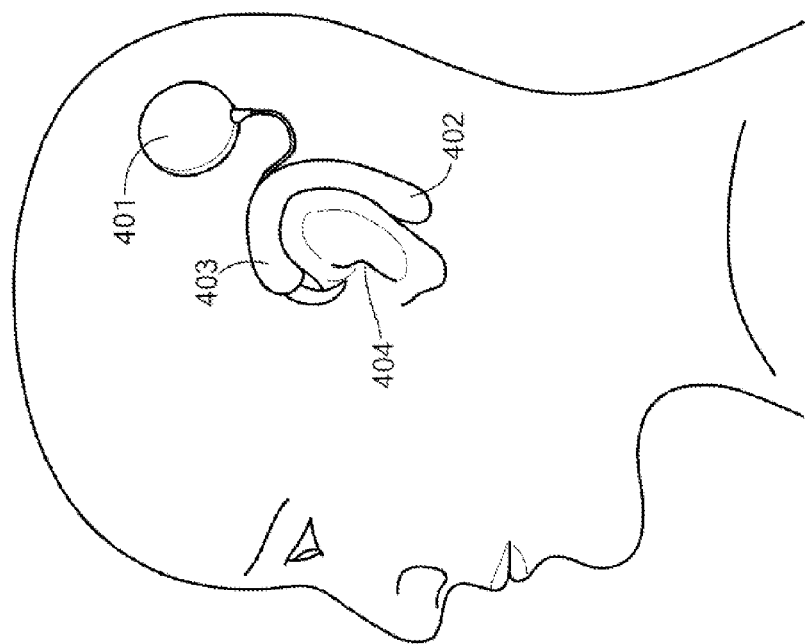
FIG. 4 shows some of the external components of one specific embodiment.

The external processor 201 in turn processes the external movement signal to generate an implant communication signal that includes a signal component based on the external movement signal and an electrical power component that provides electrical power for implanted system components (e.g. from a battery arrangement within the external processor 201). The implant communication signal from the external processor 201 is transmitted across the skin by an external transmitter coil 202 to a corresponding implant receiver coil 203. FIG. 4 shows the appearance of the external components in another similar embodiment where an external signal processor 403 and external battery power supply 402 hook onto the outer ear of the user, with a flexible cable 404 connecting to an external motion sensor arrangement in the ear canal and an external transmitter coil 401 magnetically positioned on the scalp of the user over a corresponding implanted receiver coil.

An implant processor 206 is implanted under the skin and coupled to the implant receiver coil 203. The implant processor 206 contains an internal movement sensor that generates an internal movement signal representing movement of the patient's head. The implant processor 206 processes the implant communication signal to extract its signal component (from the external movement sensor 208) and also has available the internal movement signal from the internal movement sensor. From these, the implant processor 206 generates an implant stimulation signal based on one of the movement signals to vestibular stimulator electrodes 205 that electrically stimulate target neural tissue such as the semicircular canals 106, 107, 108 of the vestibular labyrinth 105, one or both otolith organs and/or the vestibular nerve 111 or ganglion for vestibular sensation by the patient as a balance signal.

Figure 3:
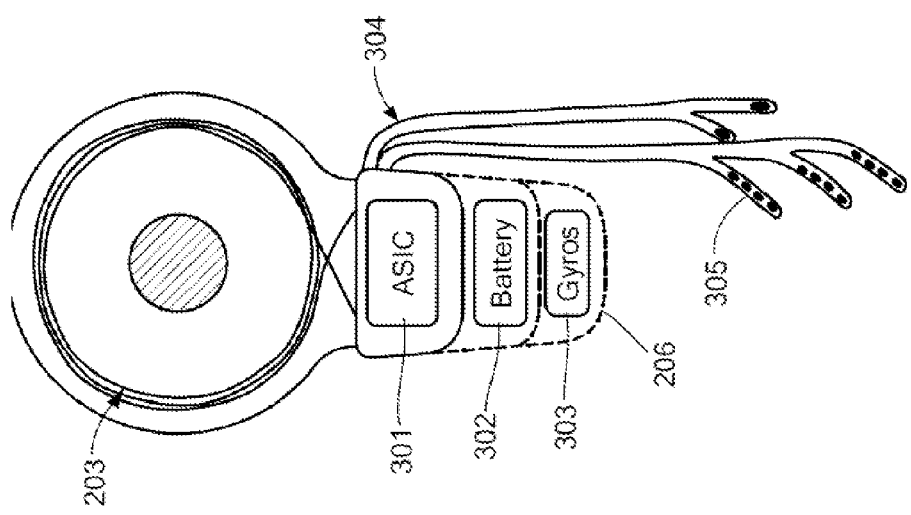
FIG. 3 shows one arrangement for an implant processor for use in embodiments of the present invention.

FIG. 3 shows structural details of an implant housing 300 which includes a receiver coil 203 and an implant processor 206. A custom ASIC 301 in the implant processor 206 provides the processing functionality for producing the implant stimulation signal, e.g., sequences of multiphasic pulses of varying amplitude/duration and/or repetition frequency using bipolar or monopolar stimulation, using single channel or multi-channel stimulation to the vestibular stimulation electrodes 305 that are connected to the implant housing 300. The implant processor 206 may preferentially base the implant stimulation signal on the external movement signal when it is available, and otherwise may use the internal movement signal. Or in some embodiments, the implant processor 206 may preferentially base the implant stimulation signal on the internal movement signal when the external movement signal exceeds some acceptable threshold value. In some embodiments, the implant processor 206 also may include a baseline pacing mode wherein the implant stimulation signal is generated without reference to a movement signal. The embodiment shown in FIG. 3 also has a separate reference electrode lead 304 that is useful for the case of monopolar stimulation pulses. Also contained within the implant housing 300 shown in FIG. 3 is the implant power supply 302 (e.g., a rechargeable battery) that extracts the power component from the received implant communications signal, and powers the implant when the external components are not attached.

The implant housing 300 also contains the internal movement sensor 303, for example, a digital gyroscope array. The internal movement sensor 303 may require less rotational sensitivity (in terms of number of degrees per second) than the external movement sensor, and therefore, may also need less power. Consequently, the system power source (either in the external portion or an implantable battery) could operate the system for a longer time until recharging or change of batteries is required.

Embodiments are not limited to locating the external movement sensor within the ear canal. For example, some embodiments may be based on a button housing processor that is positioned and stabilized on the scalp of the user in a fixed desired position over the implanted device where the risk of being moved or falling off is relatively low. This suggests a button housing device 600 such as the embodiment shown in FIG. 6 that contains a disposable or rechargeable battery or battery array 601, a transmitter coil 604, one or more external movement sensor devices 602 (e.g., gyroscope arrays), an external signal processor 605 and a positioning arrangement 603 (e.g., an external holding magnet that cooperates with an implanted positioning magnet). The embodiment shown in FIG. 6 also includes a pressure operated control switch 606 which the user can use to control operation of the button housing device 600 and/or which can also switch an in the ear device such as those described above. Unlike the earlier in the ear canal arrangements, a button housing device 600 as shown in FIG. 6 requires no cable and may therefore have less chance of being displaced in normal usage.

In button housing type embodiments, the implanted device can usefully include a rechargeable implant battery that can provide the implanted components with enough electrical energy for at least some minutes of operation so that the external button housing device 600 can be taken off for maintenance such as exchanging the battery, or for showering, etc. In some embodiments, the battery for the external button housing device 600 may be placed in a separate housing which is connected by a cable to the external button housing device 600. In some embodiments, the external button housing device 600 may have a rechargeable battery that can be recharged via an additional charger coil which is temporarily placed over the device (e.g., for about one hour) either during normal system operation or with a special recharge mode during which time the implant uses its own batteries.

Figure 5:
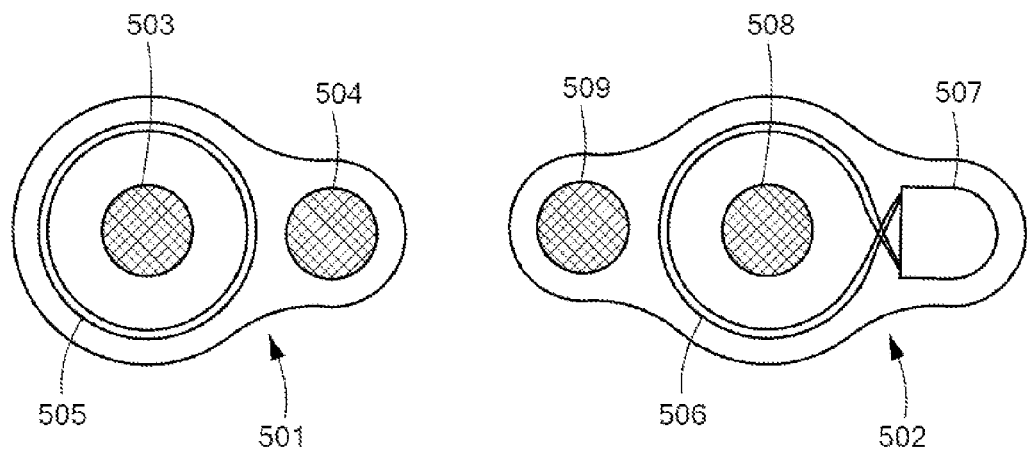
FIG. 5 shows a top view of various components associated with a scalp attached external movement sensor.
Figure 6:
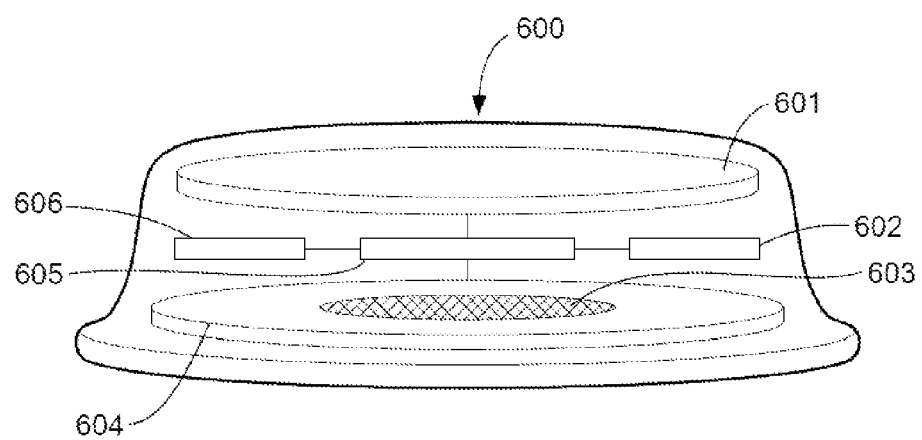
FIG. 6 shows a cross-sectional view of one specific scalp-attachable external movement sensor arrangement using two attachment magnets.

The embodiment shown in FIG. 6 is based on use of a single external holding magnet, but other embodiments such as the one shown in FIG. 5 may usefully include an additional secondary retaining magnet for both implanted part and processor such as is described in U.S. Pat. No. 6,348,070 (incorporated herein by reference). In FIG. 5, the external device housing 501 includes the usual main holding magnet 503 centered within an external transmitter coil 505 which cooperates with a corresponding implant holding magnet 508 centered within an implant receiver coil 506 in an implant device 502 which also includes an implant processor and (optional)) movement sensors 507. Offset from the main arrangement in the external device housing 501 is another secondary holding magnet 504 that cooperates with a corresponding implant secondary magnet 509 to provide an increased strength fixation of the external device housing 501 in a desired position over the implant device 502. The magnetic arrangement shown also reduces the likelihood of rotation of the external device housing 501 to the user's head.

Figure 7:
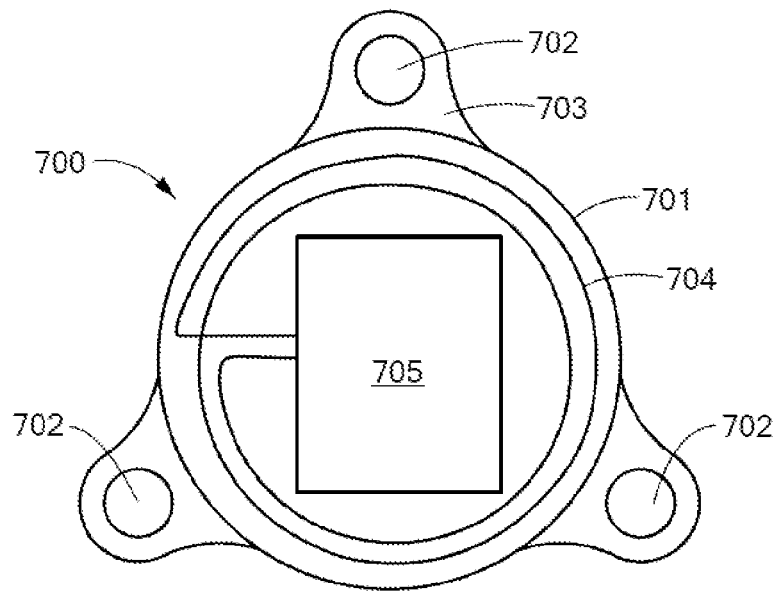
FIG. 7 shows an embodiment of an external movement sensor using three attachment magnets.

FIG. 7 shows another embodiment of an external device 700 having a device housing 701 that includes a triangular arrangement of three external holding magnets 702 that cooperate with a corresponding triangular holding magnet arrangement in the implanted device. This triangular arrangement of three external holding magnets 702 provides a very strong and stable magnetic fixation of the external device 700 over the implant device that also reliably prevents rotation of the device relative to the head. Such embodiments also provide a higher inductive link coefficient of power since there is no magnet in the center of the transmitter coil 704 which can absorb energy. An electronics package 705 within the device housing 701 includes one or more external movement sensors, a signal processor device and power supply. It may be advantageous if the device base 703 is made of a soft material that is bio-compatible and conforms easily to attach to the curved surface of the user's scalp.

Figure 9A:
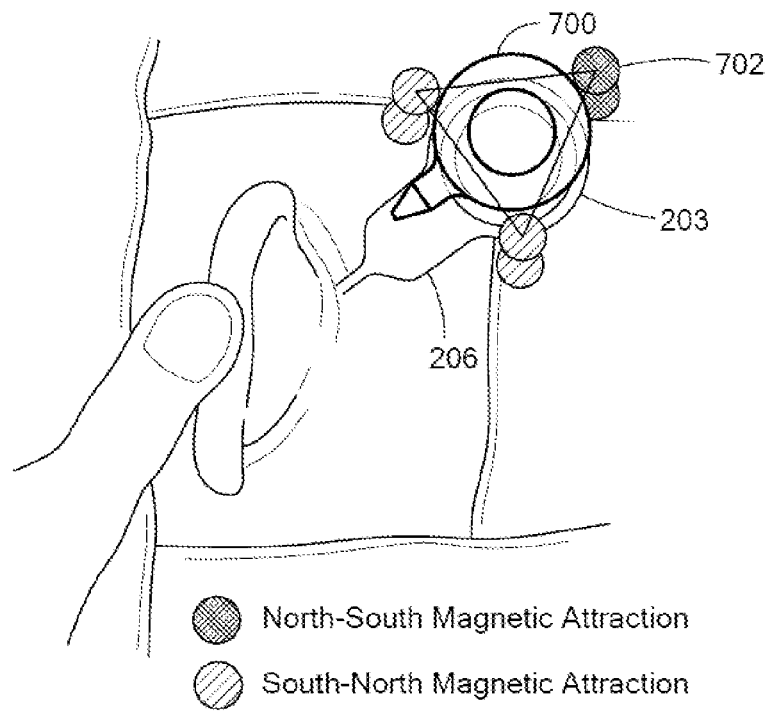
FIG. 9 A-D shows placement details of an embodiment of an external movement sensor using three symmetrical attachment magnets.
Figure 9B:
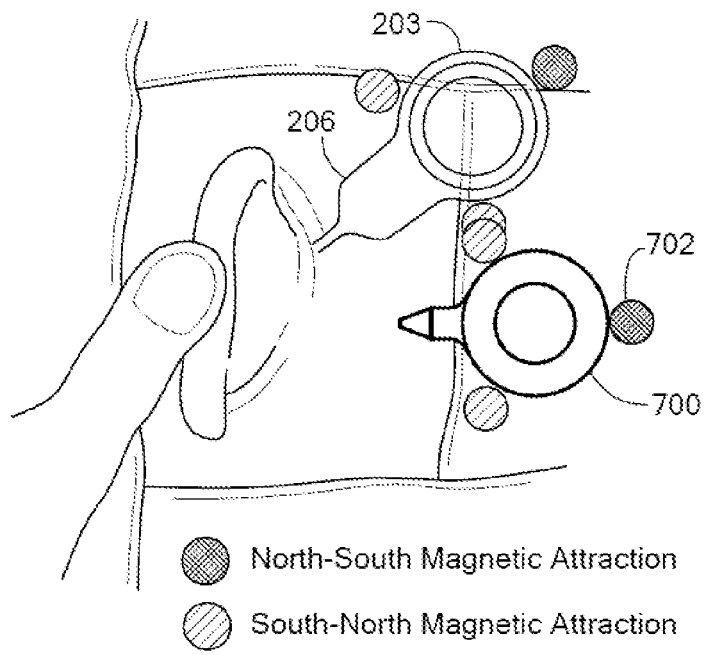
Figure 9C:
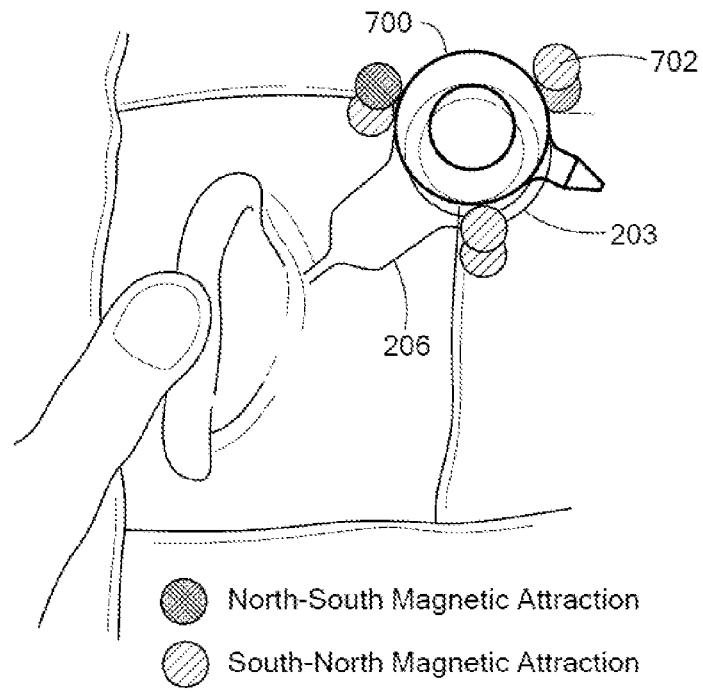
Figure 9D:
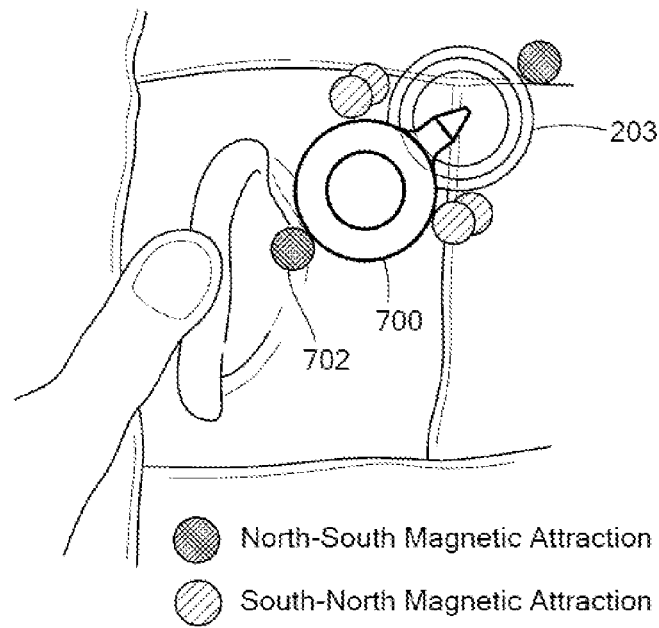
Figure 10A:
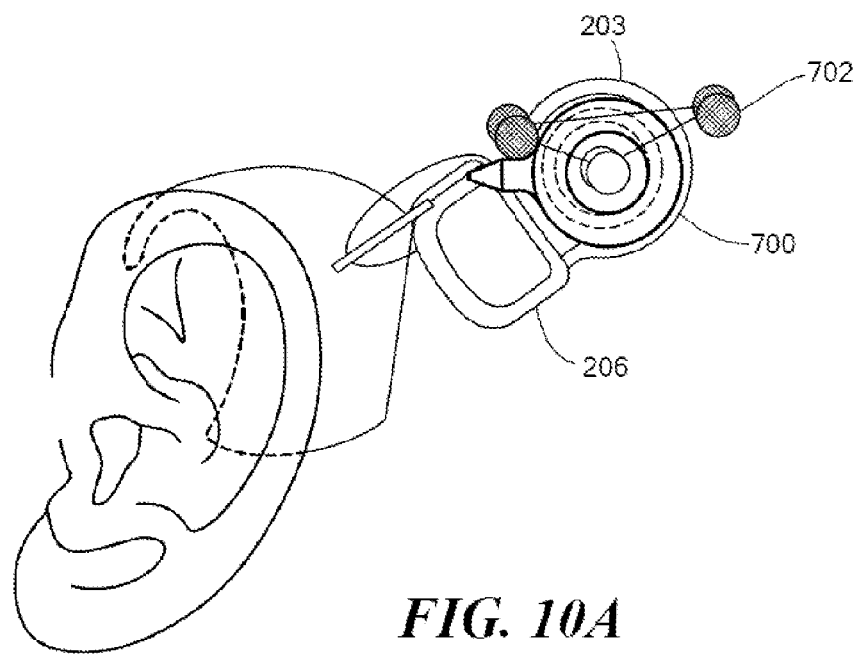
FIG. 10 A-D shows placement details of an embodiment of an external movement sensor using three asymmetrical attachment magnets.
Figure 10B:
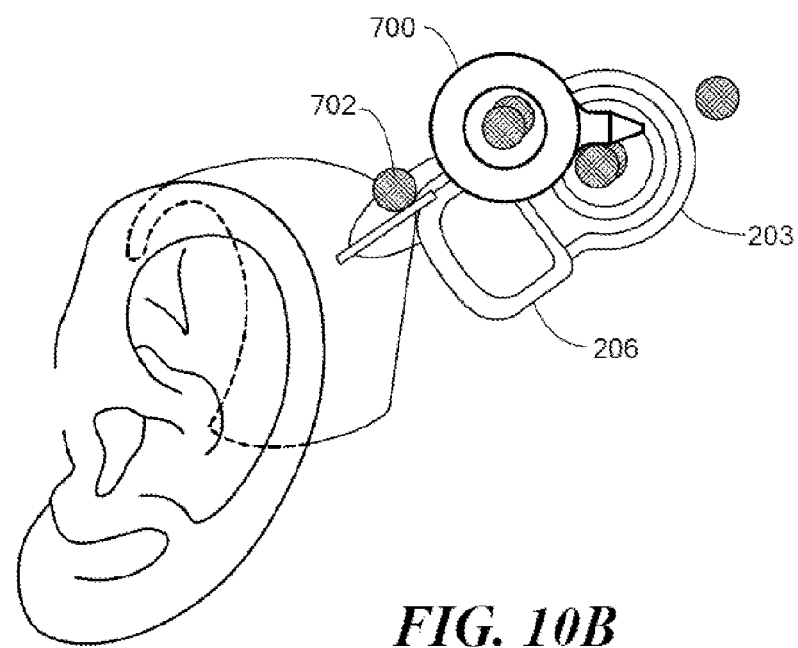
Figure 10C:
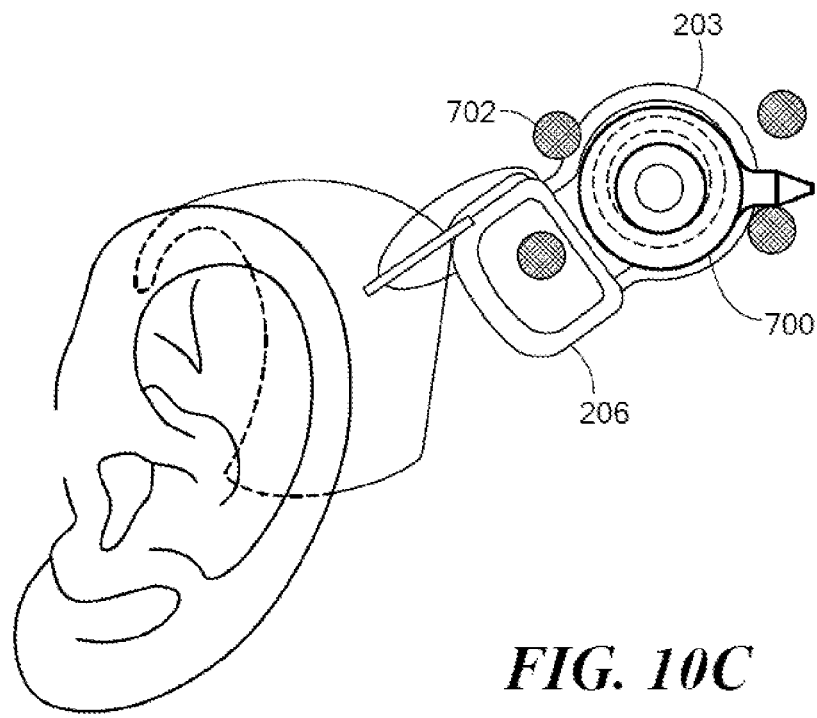
Figure 10D:
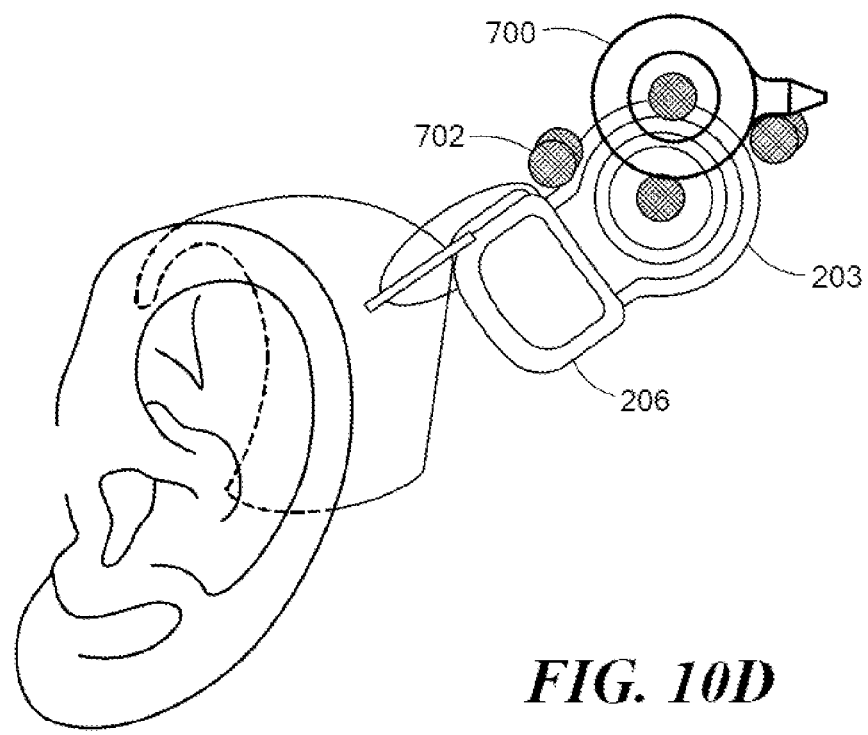

Introducing some form of asymmetry into the arrangement of the external holding magnets 702 of the external device 700 can help ensure that the external device 700 is held in a correct position over the implant. For example, FIG. 9 A-D shows placement details of an embodiment of an external device 700 using three external holding magnets 702 arranged in an equilateral triangle with an asymmetry of the magnet axial polarities (north vs. south). In FIG. 9A, the left hand and bottom external holding magnets 702 are shown with south-north outward magnetic direction, while the right hand external holding magnet 702 is shown with a north-south outward magnetic direction. In FIG. 9A, the external device 700 is correctly oriented over the implanted receiver coil 203 and implant processor 206 to allow proper coupling of the communications signal into the implant. FIG. 9B shows an incorrect attempt to place the external device 700 only a single pair holding magnets are attracting and two pairs of magnets are not magnetically engaged. In this orientation, there will be no coupling of the communications signal and the force holding the external device 700 next to the skin will be far weaker than normal so that the user should be able to detect the improper engagement. FIG. 9C shows another incorrect placement attempt where the external device 700 is properly centered over the implant receiver coil 203 to allow coupling of the communications signal, but only one magnetic pair is engaged with magnetic attraction and the other two pairs are repelling—this improper orientation requires manual force to hold the external device in position, and again, the user will know that is wrong. FIG. 9D shows yet another type of incorrect placement attempt of the external device 700 with two magnetic pairs attracting and one pair not magnetically engaged—again, there will be no coupling of the communications signal. Thus the asymmetry of magnetic polarities ensures that the user will easily detect whether or not the external device 700 is correctly oriented and properly held in place.

Besides using different axial orientations of magnetic polarities (north pole facing up vs. facing down) asymmetric arranging of pairs of holding magnets can also be achieved in other ways such as by:
  using different diametrical orientations of holding magnets
  using different distances between any two pairs of holding magnets
  using holding magnets of low magnetic attraction force thus requiring more than one pair being correctly placed to each other to hold the external over the implant. For example, FIG. 10 A-D shows placement details of an embodiment of an external movement sensor using three external magnets 702 with identical axial magnetic polarities arranged in an irregular triangle, i.e., with spatial asymmetry.

Figure 8:
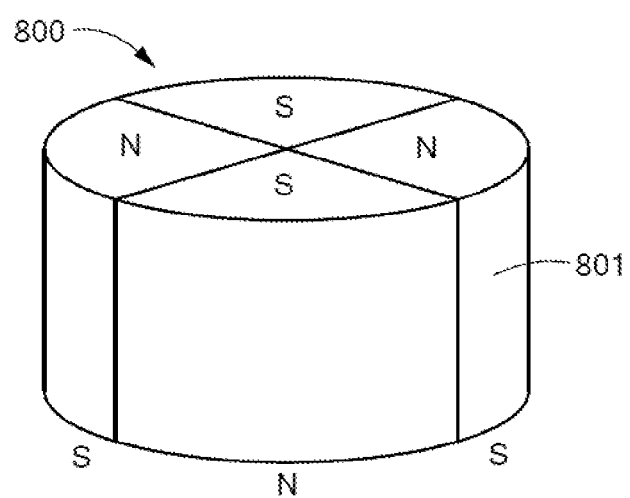
FIG. 8 shows a sectorized attachment magnet for use in embodiments of the present invention.

FIG. 8 shows another arrangement useful for a holding magnet in any of the above embodiments. That is, holding magnet 800 is divided into multiple different magnetic sectors 801 such that adjacent sectors are magnetized differently. In the example shown in FIG. 8, the magnetic sectors 801 are in the specific form of pie shaped segments but other specific shapes may also be useful. Again the advantage of such an arrangement is to help avoid relative movements or rotations of the external device relative to the head of the patient which could generate inaccurate movement sensor signals.

As explained above, the sensor elements in the external and internal movement sensors might typically be digital gyroscope arrays or digital accelerometers such as MEMS accelerometers. Small movements such as from the user pulling out or pushing in the external device or by unintended movement within the ear canal (e.g., small slippage, rotation, jaw movements) can compensated for by the location and effectiveness of the holding magnet arrangement in restoring the correct position of the external device. Some embodiments may also use a fail-safe sensor device for detecting small movements either relative to the head, or to a passive component located in the ear canal (e.g., magnet or small metal plate), or to the implant itself. When activated by such relative movement this fail-safe sensor device could either:
  (a) Signal the implant to revert to a baseline pacing mode of operation to which the patient is acclimatized,
  (b) Switch the implant off,
  (c) Apply a correction signal to the implant for small movements relative to the body which would be modify (e.g., be subtracted from) the gyroscope-based sensor movement signal until the relative movement became too large to correct for, and/or
  (d) Excessive movement of the external movement sensor device relative to the body would signal to the implant to temporarily revert to its internal movement sensor device.

The sensing elements may be based on any one of several known sensing methodologies such as electromagnetic, optical or Hall effect sensing. For example, an electromagnetic field sensing arrangement may sense the electric field in a search coil based on proximity to a small implanted coil or other metal piece while a transmitter coil generates a sensing field (like in a metal detector or eddy current sensing).

Or a movement sensing arrangement may be based on a transcutaneous light transmission system where a light source (having a frequency that transmits well through body tissue and the materials of the device) would be directed at the implanted magnet (or a non-magnetic reflector) that would be coated with a surface of high reflectance. Movement of the light source relative to the magnet/reflector would change the amount of reflected light thereby signaling movements in the device's position relative to the implanted plate.

Or embodiments may have movement sensors using Hall Effect sensing. During the implantation procedure, the surgeon can implant a second small permanent sensor magnet under the skin deep in the ear canal. Then, a two- or three-axis system of Hall Effect sensors could detect changes in the exact position of the sensor magnet relative to the device, and thereby the position of the gyroscope relative to the head. In some embodiments, a single micro three-axis sensor that works at a low enough current might be used to make corrections to the movement signal applied to the implant. The sensor array would be placed in a location of relatively high field gradient, for example, to one side of the implanted magnet.

Capacitive sensing could also provide the basis for the movement sensor elements. The portion of the external motion sensor inserted into the ear canal could contain a magnet to align it over an implanted magnet, and a capacitive sensor could then be used to indicate proximity of the device to the magnet and detect displacement of the device (up to about 2 mm) This might be useful as either a switch or as a measure of relative position and/or speed/acceleration of changes in relative position.

Some embodiments may also include a magnetically activated mechanical switch (like a magnetic reed switch) to deactivate power to one or more system components when the ear canal device is removed, or to switch the system to control of the (optional) implanted movement sensors or to a backup (pacing) mode. Some embodiments also may avoid continuous high sensor currents by using a power control switch activated by movement relative to an implanted magnet (e.g., using eddy current or capacitive sensing). The movement could then be tracked by a three-axis Hall Effect (or other) sensor arrangement so that power to monitor the relative movements would only be needed once movement was initiated. A similar relative movement sensing arrangement might also be useful in other locations around the head, such as an arrangement having magnet-based fixation somewhere external to the ear canal. Or an inductive sensing circuit could measure the frequency of an inductive link which changes when the external part is moved or removed.

Some embodiments may further include a sensor position sensor for generating a sensor movement signal representing movement of the external sensor relative to the patient's head. The system may use this information to modify one or more of the other movement signals that encode head movements. For example, this may be useful during power-up of the internal sensor as control is transferred, or for modes using a stand-alone external sensor.

Embodiments of the present invention such as those described above can be developed based on existing technologies and components. Moreover, the external components such as the gyroscope sensors can be readily accommodated. The overall system is also robust against failure of some of the internal components. In applications as a vestibular stimulation device only without additional hearing functionality, the external components would not need an opening for a microphone. As a result, the external components can be sealed to be waterproof (or at least more water resistant). In addition, there is design-inherent safety by preventing implant stimulation if the external unit is not oriented correctly on top of the implant.

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web).

Although various exemplary embodiments of the invention have been disclosed, it should be apparent to those skilled in the art that various changes and modifications can be made which will achieve some of the advantages of the invention without departing from the true scope of the invention.

What is claimed is:

1. A partially implantable vestibular prosthesis system comprising:
   one or more external movement sensors attachable to the skin of a patient's head and configured to generate an external movement signal representing movement of the patient's head;
   an external transmitter in communication with the external movement sensor configured for transcutaneous transmission of an implant communication signal having an electrical power component and a signal component based on the external movement signal;
   a fail-safe sensor configured to detect movement of the one or more external movement sensors relative to the head and generate a corresponding relative motion signal; and
   an implant processor implantable under the skin and in communication with the fail-safe sensor and the external transmitter and configured to generate an implant stimulation signal based on the external movement signal and/or the relative motion signal to electrically stimulate target neural tissue for vestibular sensation by the patient.

2. A system according to claim 1, wherein the one or more external movement sensors includes an ear canal external movement sensor configured to be attachable within the ear canal of the patient's head.

3. A system according to claim 2, wherein the ear canal external movement sensor is configured to be magnetically attachable within the ear canal over a corresponding implanted holding magnet which establishes a correct position for the external movement sensor.

4. A system according to claim 2, wherein the ear canal external movement sensor is configured to leave a portion of the ear canal unoccluded to allow hearing sensation by the tympanic membrane.

5. A system according to claim 1, wherein the one or more external movement sensors is configured to be magnetically attachable on the scalp of the patient's head over a corresponding implant magnet arrangement which establishes a correct position for the external movement sensor.

6. A system according to claim 5, wherein the one or more external movement sensors includes a plurality of magnets for cooperation with a corresponding plurality of magnets in the implant magnet arrangement.

7. A system according to claim 6, wherein the plurality of magnets in the one or more external movement sensor are arranged with asymmetrical magnetic polarities.

8. A system according to claim 6, wherein the plurality of magnets in the one or more external movement sensors are arranged with spatial asymmetry.

9. A system according to claim 6, wherein the plurality of magnets in the one or more external movement sensors are arranged with asymmetrically different diametrical orientations.

10. A system according to claim 6, wherein the plurality of magnets in the one or more external movement sensors are arranged with asymmetrically different distances between cooperating pairs of magnets.

11. A system according to claim 6, wherein the plurality of magnets in the one or more external movement sensors are arranged to require orientation of the external movement sensor so that each magnet in the external movement sensor is cooperating with another corresponding magnet in the implant magnet arrangement in order to have enough magnetic attraction force to securely hold the external movement sensor.

12. A system according to claim 1, wherein the fail-safe sensor comprises a sensor position sensor configured to generate a sensor movement signal representing movement of the external sensor relative to the patient's head.

13. A system according to claim 1, wherein the implant processor includes a baseline pacing mode wherein the implant stimulation signal is generated without reference to a movement signal.

14. A system according to claim 1, wherein the target neural tissue includes the semicircular canals of the inner ear.

15. A system according to claim 1, wherein the target neural tissue includes the vestibular nerve.

\* \* \* \* \*